United States Patent [19]

Malle

[11] Patent Number: 5,935,558
[45] Date of Patent: *Aug. 10, 1999

[54] COSMETIC COMPOSITION CONTAINING AN N-MERCAPTOALKYLALKANEDIAMIDE OR ONE OF ITS COSMETICALLY ACCEPTABLE SALTS AS REDUCING AGENT

[75] Inventor: Gérard Malle, Meaux, France

[73] Assignee: L'Oreal, SA, France

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/866,099

[22] Filed: May 30, 1997

Related U.S. Application Data

[63] Continuation of application No. 08/337,119, Nov. 10, 1994, Pat. No. 5,700,454.

[30] Foreign Application Priority Data

Nov. 12, 1993 [FR] France .................................. 93-13517

[51] Int. Cl.⁶ ................................ A61K 7/09; A61K 7/06
[52] U.S. Cl. .................... 424/70.1; 424/70.4; 424/70.51; 424/70.1

[58] Field of Search .................................. 424/70.1, 70.2, 424/70.4, 70.51

[56] References Cited

U.S. PATENT DOCUMENTS

| | | |
|---|---|---|
| 4,112,119 | 9/1978 | Ondetti et al. . |
| 4,513,009 | 4/1985 | Roques et al. . |
| 5,085,860 | 2/1992 | Junino et al. . |
| 5,154,918 | 10/1992 | Maignan et al. . |
| 5,334,377 | 8/1994 | Junino et al. . |

FOREIGN PATENT DOCUMENTS

| | | |
|---|---|---|
| 0038758 | 10/1981 | European Pat. Off. . |
| 0161769 | 11/1985 | European Pat. Off. . |
| 0432000 | 6/1991 | European Pat. Off. . |
| 0465342 | 1/1992 | European Pat. Off. . |
| 0514282 | 11/1992 | European Pat. Off. . |
| 2669329 | 5/1992 | France . |

Primary Examiner—Sally Gardner-Lane
Attorney, Agent, or Firm—Finnegan, Henderson, Farabow, Garrett & Dunner, L.L.P.

[57] ABSTRACT

A cosmetic composition for the first step of an operation for the permanent deformation of hair, the composition containing an N-mercaptoalkylalkanediamide or one of its cosmetically acceptable salts as a reducing agent, including new N-mercaptoalkylalkanediamide disulphides and new N-mercaptoalkylalkanediamides, and its use in a process for the permanent deformation of hair.

16 Claims, No Drawings

COSMETIC COMPOSITION CONTAINING AN N-MERCAPTOALKYLALKANEDIAMIDE OR ONE OF ITS COSMETICALLY ACCEPTABLE SALTS AS REDUCING AGENT

This is a continuation of application Ser. No. 08/337,119, filed Nov. 10, 1994, now U.S. Pat. No. 5,700,454.

The present invention relates to a cosmetic composition for the first step of an operation for the permanent deformation of hair, the composition containing an N-mercaptoalkylalkanediamide or one of its cosmetically acceptable salts as reducing agent, and to its use in a process for permanent deformation of hair. The present invention also relates to new N-mercaptoalkylalkanediamide disulphides and new N-mercaptoalkylalkanediamides, as well as to a process for making N-mercaptoalkylalkanediamides.

The technique for carrying out the permanent deformation of hair comprises, in a first step, opening the disulphide bonds of keratin (cysteine) with the aid of a composition containing a reducing agent (reduction stage), and then, preferably after having rinsed the hair, reconstituting the disulphide bonds in a second step by applying to the hair under tension an oxidizing composition (oxidation stage, also called fixing stage) so as to impart the required form to the hair. This technique makes it possible equally well to produce either the waving of hair or its straightening or its uncrinkling.

The compositions for carrying out the first step of a permanent-waving operation are generally in the form of lotions, creams, gels or powders to be diluted in a liquid carrier and preferably contain a thiol as reducing agent. Among the latter, those commonly employed are cysteine and thioglycolic acid, as well as its esters, especially glycerol monothioglycolate.

Thioglycolic acid is particularly effective for reducing the disulphide bonds in keratin and may be considered at alkaline pH, especially in the form of ammonium thioglycolate, as the permanent-waving reference compound. However, it exhibits the disadvantage of giving off an unpleasant odor. A perfume enabling the odors to be masked is generally used to remedy this.

Cysteine produces a much fainter odor than that of thioglycolic acid but the degree of curling obtained is much lower and far from being satisfactory. In addition, cysteine requires the use of a highly alkaline pH.

Glycerol monothioglycolate is also very malodorous. On the other hand, it is employed at a pH close to neutrality, but its performance is markedly inferior to that of thioglycolic acid.

Various investigations have been conducted with a view to overcoming the disadvantages of these reducing agents and the use of new reducing compounds has been proposed for this purpose. Thus, in European Patent Application EP-A-465,342 the use of derivatives of N-(mercaptoalkyl) succinamic acid has been described as have, furthermore, the corresponding imides.

The inventor has now found that the use of the amides of the derivatives of N-(mercaptoalkyl)succinamic acid, particularly at equivalent molarity, makes it possible to obtain curling efficiencies which are superior to those obtained with the aid of the corresponding acids and to that obtained, according to the state of the art, with the aid of thioglycolic acid. This class of amides can actually exhibit curling performance which is quite exceptional while not having the sulphurous odor specific to the thiols. However, it is well known that the higher the curling efficiency, the more the hair is damaged. Now, it has been found quite surprisingly that with these compounds the improvement in curling is obtained without damage to the state of the hair. The reducing agents of the compositions according to the invention make it possible, furthermore, to obtain a liveliness and a beauty of curling which are superior to those obtained according to the state of the art.

The subject of the invention is therefore a cosmetic composition for the first stage of an operation for permament deformation of hair wherein disulphide bonds of keratin are reduced, the composition comprising at least one compound having the following formula:

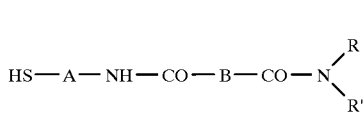
(I)

in which

A denotes the divalent radical —(CH$_2$)$_n$—, being an integer from 2 to 5, or the divalent radical —(CH$_2$)$_2$—O—(CH$_2$)$_2$—, B denotes a radical chosen from the group including:
(a) the divalent radical —(CH$_2$)$_m$—, being an integer from 1 to 7,
(b) the divalent radical

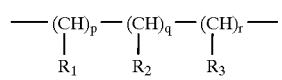

in which one of the groups R$_1$, R$_2$ and R$_3$ denotes a radical chosen from the group including linear or branched alkyl radicals containing from 1 to 4 carbon atoms, methoxymethyl, phenyl, benzyl, cyclohexyl and cyclopentyl radicals, and the other two groups are a hydrogen atom, p, q and r being 0 or an integer from 1 to 4 and 1≦p+q+r≦4, and further in which the p, q, or r corresponding to one of the groups R$_1$, R$_2$, or R$_3$ that is said radical is an integer from 1 to 4,
(c) the divalent radical

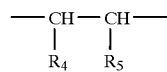

in which R$_4$ and R$_5$ either, being identical or different, denote a linear or branched alkyl radical containing from 1 to 4 carbon atoms, or, together with the adjacent carbon atoms, form a cyclohexane or cyclohexene ring, (d) the divalent radical

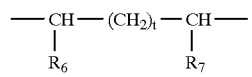

in which one of the groups R$_6$ and R$_7$ denotes an —NH$_2$ radical and the other group denotes a hydrogen atom; t being equal to 0 or 1, and (e) the divalent radical

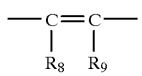

in which $R_8$ and $R_9$ either, being identical or different, denote a hydrogen atom or a linear or branched alkyl radical containing from 1 to 4 carbon atoms or, together with the adjacent carbon atoms, form a benzene ring, R and R', which are identical or different, denote:
either a hydrogen atom or a radical chosen from the group including linear or branched alkyl radicals containing from 1 to 4 carbon atoms, and linear or branched hydroxyalkyl radicals containing from 1 to 5 carbon atoms,
or R denotes a hydrogen atom and R' an aminoalkyl radical —$(CH_2)_v$—$NR_{10}R_{11}$ in which v is an integer from 1 to 3 and $R_{10}$ and $R_{11}$, which are identical or different, denote a hydrogen atom or a linear or branched alkyl radical containing from 1 to 3 carbon atoms, $R_{10}$ and $R_{11}$, being incapable of simultaneously denoting a hydrogen atom, or an organic salt or an inorganic salt of the at least one compound of formula (I).

Among the cosmetically acceptable salts of the compounds of formula (I), those particularly preferred are the hydrochlorides, hydrobromides, citrates, oxalates and acetates.

By way of preference, the hydroxyalkyl radical containing from 1 to 5 carbon atoms is chosen from the 2-hydroxyethyl, 2-hydroxypropyl, 3-hydroxypropyl, 1-hydroxymethylpropyl, 1,1-dihydroxymethylpropyl and 1,1,1-tri(hydroxymethyl)methyl radicals.

Among the preferred compounds corresponding to the formula (I) there may be mentioned especially:
when B denotes the —$CH_2$— divalent radical:
N-(2-mercaptoethyl)malonamide
N-(3-mercaptopropyl)malonamide
N-(5-mercaptopentyl)malonamide
N-(2-(2-mercaptoethoxy)ethyl malonamide
N-(2-mercaptoethyl)-N'-methylmalonamide
N-(2-mercaptoethyl)-N',N'-dimethylmalonamide
N-(2-mercaptoethyl)-N'-ethylmalonamide
N-(2-mercaptoethyl)-N',N'-diethylmalonamide
N-(2-mercaptoethyl) -N'-(2-hydroxyethyl) malonamide
N-(2-mercaptoethyl)-N',N'-(2, 2-dihydroxyethyl) malonamide
N-(2-mercaptoethyl)-N'-(3-dimethylaminopropyl) malonamide
N-(2-mercaptoethyl)-N'-(3-diethylaminopropyl) malonamide;
when B denotes the —$(CH_2)_2$— divalent radical:
N-(2-mercaptoethyl)succinamide
N-(3-mercaptopropyl)succinamide
N-(5-mercaptopentyl)succinamide
N-[2-(2-mercaptoethoxy)ethyl]succinamide
N-(2-mercaptoethyl)-N'-methylsuccinamide
N-(2-mercaptoethyl)-N',N'dimethylsuccinamide
N-(2-mercaptoethyl)-N'-ethylsuccinamide
N-(2-mercaptoethyl)-N',N'-diethylsuccinamide
N-(2-mercaptoethyl)-N'-(2-hy droxyethyl) succinamnide
N-(2-mercaptoethyl)-N',N'-(2,2-dihydroxyethyl) succinamide
N-(2-mercaptoethyl)-N'-(3-dimethylaminopropyl) succinamide N-(2-mercaptoethyl)-N'-(3-diethylaminopropyl) succinamide;
when B denotes the —$(CH_2)_3$— divalent radical:
N-(2-mercaptoethyl)glutaramide
N-(3-mercaptopropyl)glutaramide
N-(5-mercaptopentyl)glutaramide
N- [2-(2-mercaptoethoxy)ethyl)glutaramide
N-(2-mercaptoethyl)-N'-methylglutaramide
N-(2-mercaptoethyl)-N',N'-dimethylglutaramide
N-(2-mercaptoethyl)-N'-ethylglutaramide
N-(2-mercaptoethyl)-N',N'-diethylglutaramide
N-(2-mercaptoethyl)-N'-(2-hydroxyethyl) glutaramide
N-(2-mercaptoethyl)-N',N'-(2,2-dihydroxyethyl) glutaramide
N-(2-mercaptoethyl)-N(3-dimethylaminopropyl) glutaramide;
when B denotes the —$(CH_2)_4$— divalent radical:
N-(2-mercaptoethyl)adipamide
N-(2-mercaptoethyl)-N'-methyladipamide
N-(2-mercaptoethyl)-N',N'-dimethyladipamide
N-(2-mercaptoethyl)-N'-ethyladipamide
N-(2-mercaptoethyl)-N'-(2-hydroxyethyl) adipamide
N(2-mercaptoethyl)-N',N'(2,2-dihydroxyethyl) adipamide
N-(2-mercaptoethyl)-N'-(3-dimethylaminopropyl) adipamide;
when B denotes the divalent radical

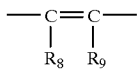

$R_8$ and $R_9$ having the same meanings as those given above:
N-(2-mercaptoethyl)fumaramide
N-(3-mercaptopropyl)fumaramide
N-(5-mercaptopentyl)fumaramide
N-[2-(2-mercaptoethoxy)ethyl]fumaramide
N-(2-mercaptoethyl)-N'-methylfumaramide
N-(2-mercaptoethyl)-N',N'-dimethylfumaramide
N-(2-mercaptoethyl)-N'-ethylfumaramide
N-(2-mercaptoethyl)-N',N'-diethylfumaramide
N-(2-mercaptoethyl)-N'-(2-hydroxyethyl) fumaramide
N-(2-mercaptoethyl)-N',N'-(2.,2-dihydroxyethyl) fumaramide
N-(2-mercaptoethyl)-N'-(3-dimethylaminopropyl) fumaramide;
N-(2-mercaptoethyl)terephthalamide
N-(2-mercaptoethyl)-N'-methylterephthalamide
N-(2-mercaptoethyl)-N'-ethylterephthalamide
N-(2-mercaptoethyl)-N'-(2-hydroxyethyl) terephthalamide
N-(2-mercaptoethyl)-N'-(3-dimethylaminopropyl) terephthalamide;
when B denotes the divalent radical —$(CH_2)_m$—, m being an integer between 6 and 7:
octanedioic acid 1-amide 5-[(2-mercaptoethyl) amide]
nonanedioic acid 1-amide 5-[(2-mercaptoethyl) amide]
when B denotes the divalent radical

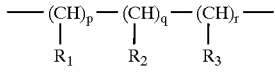

$R_1$, $R_2$, $R_3$, p, q and r having the same meanings as those given above:

3-methylpentanedioic acid 1-amide 5-[(2-mercaptoethyl) amide]

2-ethylhexanedioic acid 1-amide 6-[(2-mercaptoethyl) amide);

when B denotes the divalent radical

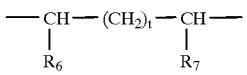

$R_6$, $R_7$ and t having the same meanings as those given above:

4-aminopentanedioic acid 1-amide 5-((2-mercaptoethyl) amide]

3-aminobutanedioic acid 1-amide 5-[(2-mercaptoethyl) amide].

In the compositions according to the invention the reducing agent of formula (I) is generally present in a concentration ranging from 0.5 to 30% and preferably from 5 to 20% by weight relative to the total weight of the reducing composition.

The pH of the composition preferably ranges from 4 to 11 and more particularly from 6 to 10 and is obtained with the aid of an alkaline agent such as, for example, aqueous ammonia, monoethanolamine, diethanolamine, triethanolamine, 1,3-propanediamine, ammonium carbamate, an alkali metal or ammonium carbonate or bicarbonate, an organic carbonate such as guanidine carbonate or an alkali metal hydroxide or with the aid of an acidifying agent such as, for example, hydrochloric acid, acetic acid, lactic acid, oxalic acid or boric acid.

The reducing composition may also contain in association another known reducing agent such as, for example, thioglycolic acid, glycerol or glycol monothioglycolate, cysteamine and its $C_1$–$C_4$-acyl derivatives such as N-acetylcysteamine or N-propionyl cysteamine, cysteine, N-acetylcysteine, sugar N-mercaptoalkylamides such as N-(2-mercaptoethyl) gluconamide, β-mercaptopropionic acid and its derivatives, thiolactic acid and its esters such as glycerol monothiolactate, thiomalic acid, pantethin, thioglycerol, alkali or alkaline-earth metal sulphites or bisulphites, the N-(mercaptoalkyl)-ω-hydroxyalkylamide described in Patent Application EP-A-354,835, the disclosure of which is hereby incorporated by reference, and the N-mono- or N,N-dialkylmercapto-4-butyramides described in Patent Application EP-A-368,763, the disclosure of which is hereby incorporated by reference, the aminomercaptoalkylamides described in Patent Application EP-A-432,000, the disclosure of which is hereby incorporated by reference, the derivatives of N-(mercaptoalkyl)succinamic acids or of N-(mercaptoalkyl)succinimides described in Patent Application EP-A-465,342, the disclosure of which is hereby incorporated by reference, the alkylaminomercaptoalkylamides described in Patent Application EP-A-514,282, the disclosure of which is hereby incorporated by reference, or the mixture of 2-hydroxypropyl thioglycolate and 2-hydroxy-1-methylethyl thioglycolate described in Patent Application FR-A-2,679,448, the disclosure of which is hereby incorporated by reference.

According to a preferred embodiment the reducing composition also contains a surface-active agent of nonionic, anionic, cationic or amphoteric type commonly employed in reducing compositions for permanent waving and, among these, it is possible to mention alkyl sulphates, alkylbenzene sulphates, alkyl ether sulphates, alkylsulphonates, quaternary ammonium salts, alkylbetaines, oxyethylenated alkylphenols, fatty acid alkanolamides, oxyethylenated fatty acid esters and other nonionic surfactants of the hydroxypropyl ether type.

When the reducing composition contains at least one surface-active agent, the latter is generally present in a maximum concentration of 30% by weight, but preferably from 0.5 to 10% by weight relative to the total weight of the reducing composition.

The reducing composition may also contain a treating agent of cationic, anionic, nonionic or amphoteric nature with the aim of improving the cosmetic properties of the hair or of diminishing or preventing its deterioration.

Among the treating agents which are particularly preferred there may be mentioned especially those described in French Patents FR-A-2,598,613 and FR-A-2,470,596, the disclosures of both of which are hereby incoporated by reference. It is also possible to employ as treating agents linear or cyclic, volatile or nonvolatile silicones and their mixtures, polydimethylsiloxanes, quaternized polyorganosiloxanes such as those described in French Patent Application FR-A-2,535,730, the disclosure of which is hereby incorporated by reference, polyorganosiloxanes containing aminoalkyl groups modified with alkoxycarbonylalkyl groups such as those described in U.S. Pat. No. 4,749,732, the disclosure of which is hereby incorporated by reference, polyorganosiloxanes such as the polydimethylsiloxanepolyoxyalkyl copolymer of the Dimethicone Copolyol type, a polydimethylsiloxane containing stearoxy end groups (stearoxydimethicone), a polydimethylsiloxane-dialkylammonium acetate copolymer or a polydimethylsiloxane polyalkylbetaine copolymer which are described in GB-A-2,197,352, the disclosure of which is hereby incorporated by reference, organopolysiloxanes modified with mercapto or mercaptoalkyl groups such as those described in French Patent FR-A-1,530,369 and in European Patent Application EP-A-295,780, the disclosures of both of which are hereby incoporated by reference, and silanes such as stearoxytrimethylsilane.

The reducing composition may also contain other treating ingredients such as cationic polymers such as those employed in the compositions of French Patents FR-A-2,472,382 and FR-A-2,495,931, the disclosures of both of which are hereby incoporated by reference, or cationic polymers of the ionene type, such as those employed in the compositions of Luxembourgian Patent 83703, the disclosure of which is hereby incorporated by reference, amino acids which are basic (such as lysine or arginine) or acidic (such as glutamic acid or aspartic acid), peptides and their derivatives, protein hydrolysates, waxes, swelling and penetrating agents making it possible to strengthen the effectiveness of the reducing agent, such as the $SiO_2$/PDMS (polydimethylsiloxane) mixture, dimethylisosorbitol, urea and its derivatives, pyrrolidone, N-alkylpyrrolidones, thiamorpholinone, alkylene glycol or dialkylene glycol alkyl ethers such as, for example propylene glycol monoethyl ether, dipropylene glycol monomethyl ether, ethylene glycol monoethyl ether and diethylene glycol monoethyl ether, $C_3$–$C_6$alkanediols such as, for example, 1,2-propanediol and 1,2-butanediol, 2-imidazolidone and other compounds such as fatty alcohols, lanolin derivatives, active ingredients such as pantothenic acid, agents against hair loss, anti-dandruff agents, thickeners, suspending agents, sequestering agents, opacifying agents, colorants, sunscreens and perfumes and preserving agents.

The reducing composition according to the invention is presented essentially in aqueous form, especially in the form of a thickened or unthickened lotion, a cream or a gel.

The reducing composition according to the invention may also be of the exothermic type, that is to say giving rise to some warming-up when applied to the hair, which is pleasing to the person undergoing the first step of the permanent waving or of the straightening.

The carrier for the compositions according to the invention is preferably water or a hydroalcoholic solution of a lower alcohol such as ethanol, propanol, isopropanol or butanol or of a polyol such as glycerol, in a maximum concentration of 20%. When the compositions are intended for a hair straightening or uncrinkling operation, the reducing composition is preferably in the form of a cream thickened so as to keep the hair as stiff as possible. These creams are produced in the form of "heavy" emulsions, for example based on glyceryl stearate, glycol stearate, self-emulsifiable waxes, fatty alcohols and the like. It is also possible to employ liquids or gels containing thickening agents such as carboxyvinyl polymers or copolymers which "bond" the hair and keep it in the smooth position during the application period.

The compositions according to the invention may also be in so-called "self-neutralizing" or "self-regulated" form, and, in this case, the compound of the formula (I) or a salt thereof is associated with at least one disulphide which is either known for its use in a reducing composition for self-neutralizing permanent waving or is derived from a compound of formula (I) or from one of its salts and corresponds to the following formula (II):

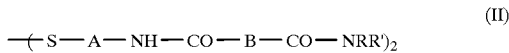

(II)

in which A, B, R and R' are independently defined as in the formula (I).

The disulphide may also be in the form of a cosmetically acceptable salt.

Among the known disulphides there may be mentioned especially dithioglycolic acid, dithioglycerol, cystamine, N,N'-diacetylcystamine, cystine, pantethine and the disulphides of the N(mercaptoalkyl)-ω-hydroxyalkylamides described in European Patent Application EP-A-354,835, the disclosure of which was incorporated by reference above, the disulphides of the N-mono- or N,N-dialkylmercapto-4-butyramides described in Patent Application EP-A-368,763, the disclosure of which was incorporated by reference above, the disulphides of the aminomercaptoalkylamides described in Patent Application EP-A-432,000, the disclosure of which was incorporated by reference above, the disulphides of the derivatives of the N-(mercaptoalkyl)succinamic acids or of the N-(mercaptoalkyl)succinimides described in Patent Application EP-A-465,342, the disclosure of which was incorporated by reference above, and the disulphides of the alkylaminomercaptoalkylamides described in Patent Application EP-A-514,282, the disclosure of which was incorporated by reference above.

Among the disulphides of formula (II) there may be mentioned:
  when B denotes the —CH$_2$— divalent radical:
    the disulphide of N-(2-mercaptoethyl)malonamide
    the disulphide of N-(3-mercaptopropyl)malonamide
    the disulphide of N-(5-mercaptopentyl)malonamide
    the disulphide of N-[2-(2-mercaptoethoxy)ethyl]malonamide
    the disulphide of N-(2-mercaptoethyl)-N'-methylmalonamide
    the disulphide of N-(2-mercaptoethyl)-N',N'-dimethylmalonamide
    the disulphide of N-(2-mercaptoethyl)-N'-ethylmalonamide
    the disulphide of N-(2-mercaptoethyl)-N',N'-diethylmalonamide
    the disulphide of N-(2-mercaptoethyl)-N'-(2-hydroxyethyl)malonamide
    the disulphide of N-(2-mercaptoethyl)-N',N'-(2,2-dihydroxyethyl)malonamide
    the disulphide of N-(2-mercaptoethyl)-N'-(3-dimethylaminopropyl)malonamide
    the disulphide of N-(2-mercaptoethyl)-N'-(3-diethylaminopropyl)malonamide;
  when B denotes the —(CH$_2$)$_2$— divalent radical:
    the disulphide of N-(2-mercaptoethyl)succinamide
    the disulphide of N-(3-mercaptopropyl)succinamide
    the disulphide of N-(5-mercaptopentyl) succinamide
    the disulphide of N-[2-(2-mercaptoethoxy)ethyl]succinamide
    the disulphide of N-(2-mercaptoethyl)-N'-methylsuccinamide
    the disulphide of N-(2-mercaptoethyl)-N'-(2-hydroxyethyl)succinamide
    the disulphide of N-(2-mercaptoethyl)-N'-(3-dimethylaminopropyl)succinamide;
  when B denotes the —(CH$_2$)$_3$— divalent radical:
    the disulphide of N-(2-mercaptoethyl)glutaramide;
  when B denotes the —(CH$_2$)$_4$— divalent radical:
    the disulphide of N-(2-mercaptoethyl)adipamide.

In the self-neutralizing compositions the disulphide is generally present in a molar ratio of 0.5 to 2.5 and preferably of 1 to 2 relative to the compound of formula (I) or its salts (see U.S. Pat. No. 3,768,490, the disclosure of which is hereby incorporated by reference).

Another subject of the present invention is a process for the permanent deformation of hair comprising, in a first stage, reducing the disulphide bonds of keratin by application, for preferably approximately 5 to 60 minutes, of a reducing composition as defined above and then, in a second stage, in re-forming the said bonds by the application of an oxidizing composition or optionally by allowing atmospheric oxygen to act.

A further subject of the present invention is a process for waving hair, in which a reducing composition as defined above is applied to wetted hair previously wound onto rollers from 4 to 20 mm in diameter, it being possible for the composition to be optionally applied progressively as the hair is wound on; the reducing composition is preferably then allowed to act for a period of 5 to 60 minutes, more preferably from 5 to 30 minutes, it is then rinsed copiously, after which an oxidizing composition is applied to the wound hair, allowing the disulphide bonds of keratin to re-form during an application period of preferably 2 to 10 minutes. After the rollers have been removed the hair is rinsed copiously.

The oxidation or oxidizing composition is of the type commonly employed and contains, as oxidizing agent, aqueous hydrogen peroxide, an alkali metal bromate, a persalt, a polythionate or a mixture of alkali metal bromate and persalt. The concentration of aqueous hydrogen peroxide may vary from 1 to 20 volumes, i.e., from 0.3% by weight to 6% by weight of the composition, and more preferably varies from 1 to 10 volumes, i.e., from 0.3% by weight to 3% by weight of the composition. The concentration of alkali metal bromate may vary from 2 to 12% and that of persalt from 0.1 to 15% by weight relative to the total weight of the oxidizing composition. The pH of the oxidizing composition generally ranges from 2 to 10. This oxidation may be performed immediately or may be delayed.

Another subject of the present invention is a process for straightening or uncrinkling hair in which a reducing composition according to the invention is applied to hair and the hair is then subjected to a mechanical deformation allowing it to be fixed in its new shape by an operation of smoothing the hair with a large-toothed comb, with the back of a comb or manually. After an application period of preferably 5 to 60 minutes, more preferably 5 to 30 minutes, a new smoothing is then performed, followed by careful rinsing and an oxidizing or fixing composition as defined above is applied, which is left to act for approximately 2 to 10 minutes and the hair is then rinsed copiously.

Another subject of the invention is the process for the preparation of the N-mercaptoalkylalkanediamides of formula (I). This process consists in reacting an aminothiol (1) with a monoester of a diacid (2) so as to obtain an N-mercaptoalkylamide ester (3) which, on treatment with a primary or secondary amine or with aqueous ammonia, produces the N-mercaptoalkylalkanediamides of formula (I) according to the following reaction scheme:

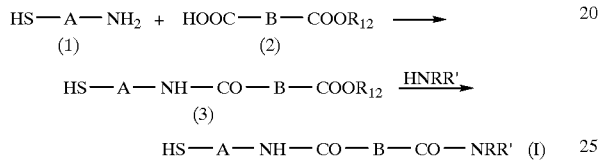

The reaction between the aminothiol (1) and the diacid monoester (2) is preferably conducted under inert atmosphere in an inert solvent such as, for example, dichloromethane, 1,2-dichloroethane, 1,1,1-trichloroethane, chloroform, acetonitrile, toluene, dioxane, tetrahydrofuran, 1,2-dimethoxyethane, cyclohexane or a mixture of these solvents, at ambient temperature in the presence of agents promoting coupling, such as dicyclohexylcarbodiimide. The radical $R_{12}$ is an alkyl residue preferably containing from 1 to 4 carbon atoms, advantageously methyl or ethyl. A, B, R and R' are independently defined as in the formula (I). The aminothiol (1) is preferably reacted in the form of its hydrochloride and, in this case, an equivalent of a base such as, for example, triethylamine is added to the reaction mixture.

The reaction of amidification of the compound (3) with a primary or secondary amine is conducted either without solvent or in the presence of a solvent such as a linear or branched lower alcohol such as, for example, methanol, at a temperature preferably between the ambient temperature and the boiling point of the alcohol employed. The reaction of amidification of the compound (3) with aqueous ammonia is carried out either with gaseous ammonia in an inert solvent or advantageously with the aid of an aqueous solution of aqueous ammonia at ambient temperature.

The disulphides of the compounds of formula (I) are obtained in a conventional manner by oxidation of the compounds of formula (I) either in air or with the aid of known oxidizing agents such as, for example, aqueous hydrogen peroxide, optionally in the presence of metal salts such as, for example, ferrous salts.

Another subject of the present invention is the new disulphides of formula (II) which follows:

$$-(-S-A-NH-CO-B-CO-NRR')_2 \qquad (II)$$

in which A, B, R and R' are independently defined as in the formula (I), or an organic salt or an inorganic salt of the said compound of formula (II).

A further subject of the present invention is the new N-mercaptoalkylalkanediamides of formula (III) which follows:

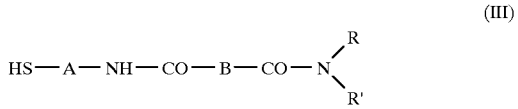

in which
A denotes the divalent radical $(CH_2)_n-$, n being an integer from 2 to 5, or the divalent radical $-(CH_2)_2-O-CH_2)_2-$,
B denotes a radical chosen from the group including:
  (a) the divalent radical $-(CH_2)_m-$, m being an integer from 1 to 7,
  (b) the divalent radical

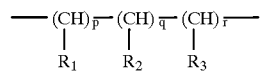

in which one of the groups $R_1$, $R_2$ and $R_3$ denotes a radical chosen from the group including linear or branched alkyl radicals containing from 1 to 4 carbon atoms, methoxymethyl, phenyl, benzyl, cyclohexyl and cyclopentyl radicals, and the other two groups are a hydrogen atom, p, q and r being 0 or an integer from 1 to 4 and $1<p+q+r<4$, and further in which the p, q, or r corresponding to one of the groups $R_1$, $R_2$, or $R_3$ that is said radical is an integer from 1 to 4,
  (c) the divalent radical

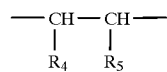

in which $R_4$ and $R_5$ either, being identical or different, denote a linear or branched alkyl radical containing from 1 to 4 carbon atoms, or, together with the adjacent carbon atoms, form a cylohexane or cyclohexene ring,
  (d) the divalent radical

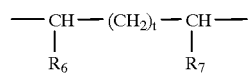

in which one of the groups $R_6$ and $R_7$ denotes an $-NH_2$ radical and the other group denotes a hydrogen atom; t being equal to 0 or 1, and
  (e) the divalent radical

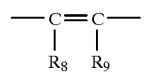

in which $R_8$ and $R_9$ either, being identical or different, denote a hydrogen atom or a linear or branched alkyl radical containing from 1 to 4 carbon atoms or, together with the adjacent carbon atoms, form a benzene ring,
R and R', which are identical or different, denote:
  either a hydrogen atom or a radical chosen from the group including linear or branched alkyl radicals containing from 1 to 4 carbon atoms, and linear or branched hydroxyalkyl radicals containing from 1 to 5 carbon atoms, or R denotes a hydrogen atom and R' an aminoalkyl radical $(CH_2)_v$-$NR_{10}R_{11}$ in which v is an integer from 1 to 3 and $R_{10}$ and $R_{11}$, which are identical or different, denote a hydrogen atom or a linear or branched alkyl radical containing from 1 to 3 carbon atoms, $R_{10}$ and $R_{11}$ being incapable of simultaneously denoting a hydrogen atom, or an organic salt or an inorganic salt of said compound of formula (III) excluding the compounds in which: either (i) A denotes the divalent radical —$(CH_2)_2$— and B denotes the radical —$(CH_2)_m$—, m being an integer from 2 to 7, or the radical

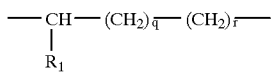

in which $R_1$ denotes a radical chosen from the group including linear or branched alkyl radicals containing from 1 to 4 carbon atoms, phenyl and benzyl radicals and, optionally, cyclohexyl and cyclopentyl radicals, <q+r<3 (synonymously 1<1+q+r<4) and R and R', which are identical or different, denote:

either a hydrogen atom or a radical chosen from the group including linear or branched alkyl radicals containing from 1 to 4 carbon atoms and, optionally, linear or branched hydroxyalkyl radicals containing from 1 to 5 carbon atoms, or R denotes a hydrogen atom and R' an aminoalkyl radical —$(CH_2)_v$—$NR_{10}R_{11}$ in which v is an integer from 1 to 3 and $R_{10}$ and $R_{11}$, which are identical or different, denote a hydrogen atom or a linear or branched alkyl radical containing from 1 to 3 carbon atoms, $R_{10}$ and $R_{11}$ not being able simultaneously to denote a hydrogen atom, or (ii) A denotes the divalent radical —$(CH_2)_2$— and B denotes the radical —$CH_2$—, or the radical

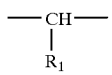

in which R1 denotes a radical chosen from the group including linear or branched alkyl radicals containing from 1 to 4 carbon atoms and methoxymethyl, phenyl and benzyl radicals, and R and R', which are identical or different, denote:

either a hydrogen atom or a radical chosen from the group including linear or branched alkyl radicals containing from 1 to 4 carbon atoms, or R denotes a hydrogen atom and R' an aminoalkyl radical —$(CH_2)_v$—$NR_{10}R_{11}$, in which v is an integer from 1 to 3 and $R_{10}$ and $R_{11}$, which are identical or different, denote a linear or branched alkyl radical containing from 1 to 3 carbon atoms.

A number of examples of preparation of compounds according to the invention and examples of reducing compositions and their use in a process for permanent deformation of hair will now be given by way of illustration, no limitation being implied.

EXAMPLE 1

Preparation of N-(2-mercaptoethyl)succinamide a) Methyl ester of N-(2-mercaptoethyl)succinamic acid 5.2 cm³ of triethylamine were added to a suspension of 4.2 g (37 mmol) of cysteamine hydrochloride in 100 cm³ of dichloromethane, stirred under argon at 0° C., followed 15 minutes later by 5.1 g of 1-hydroxybenzotriazole and, over 15 minutes, a solution of 7.63 g of dicyclohexylcarbodiimide in approximately 30 cm³ of dichloromethane. 5.15 g (38 mmol) of monomethyl succinate were then added and stirring was continued for 12 hours at ambient temperature.

The reaction mixture was filtered and the filtrate was extracted successively 3 times with 50-cm³ portions of saturated aqueous solution of sodium bicarbonate and then 3 times with 50-cm³ portions of aqueous 5% potassium bisulphate solution. The organic phase was dried over sodium sulphate and then evaporated to dryness at reduced pressure. The oil obtained was purified by chromatography on silica gel, eluted with ethyl acetate. After evaporation to dryness and drying in vacuum at ambient temperature 5.7 g of methyl ester of N-(2-mercaptoethyl)succinamic acid were obtained in the form of a colorless oil.

The 200 MHz $^1$H NMR spectrum (CDCl$_3$+TMS) and thiol determination by iodometry were consistent with the expected structure.

b) N-(2-Mercaptoethyl) succinamide

A solution of 5.7 g (30 mmol) of methyl ester of N-(2-mercaptoethyl)succinamic acid, obtained in Example 1a), in 50 cm³ of aqueous 20% solution of aqueous ammonia was stirred for 4 hours at ambient temperature under argon atmosphere.

After evaporation to dryness at reduced pressure the solid obtained was purified by recrystallization from ethanol. After filtering and drying in vacuum at 50° C. 3.8 g of N-(2-mercaptoethyl)succinamide were obtained in the form of a white solid with a melting point of 173° C.

The 200 MHz $^1$H NMR spectrum (DMSO-d$_6$+TMS) was consistent with the expected structure. The thiol determination was also consistent: found: 5.55 meq./g; calculated: 5.67 meq./g.

ELEMENTAL ANALYSIS: $C_6H_{12}N_2O_2S$

|  | C % | H % | N % | O % | S % |
| --- | --- | --- | --- | --- | --- |
| Calculated | 40.89 | 6.86 | 15.90 | 18.16 | 18.19 |
| Found | 40.75 | 6.85 | 16.25 | 18.80 | 18.11 |

EXAMPLE 2

Preparation of N-(2-mercaptoethyl)-N'-(2-hydroxyethyl)succinamide

A solution of 4.4 g (23 mmol) of methyl ester of N-(2-mercaptoethyl)succinamic acid obtained in Example 1a) in 20 cm³ of methanol, and 1.68 g (27 mmol) of ethanolamine was stirred for 5 hours at 60° C. under argon atmosphere.

After evaporation to dryness at reduced pressure and recrystallization from isopropanol 2.8 g of N-(2-mercaptoethyl)-N'-(2-hydroxyethyl)succinamide were obtained in the form of a white solid, with a melting point of 140° C.

The 200 MHz $^1$H NMR spectrum (DMSO-d$_6$+TMS) was consistent with the expected structure.

The thiol determination was also consistent: found: 4.34 meq./g; calculated: 4.54 meq./g.

ELEMENTAL ANALYSIS: $C_8H_{16}N_2O_3S$

|            | C %   | H %  | N %   | O %   | S %   |
|------------|-------|------|-------|-------|-------|
| Calculated | 43.62 | 7.32 | 12.72 | 21.79 | 14.56 |
| Found      | 43.57 | 7.29 | 12.67 | 21.85 | 14.45 |

EXAMPLE 3

Preparation of N-(2-mercaptoethyl)malonamide a) Methyl ester of N-(2-mercaptoethyl)malonamic acid 89 g of 1-hydroxybenzotriazole were added to a suspension of 75 g (0.66 mol) of cysteamine hydrochloride in 700 cm³ of dichloromethane, stirred under argon at 0° C., followed, over approximately 30 minutes, by a solution of 136 g of dicyclohexylcarbodiimide in 300 cm³ of dichloromethane. 102 g (0.65 mol) of potassium monomethyl malonate were then added and stirring was continued for 30 minutes at 0° C. and then 4 hours at ambient temperature.

The reaction mixture was filtered. The filtrate was extracted successively with an aqueous 5% solution of sodium bicarbonate, an aqueous 5% solution of potassium bisulphate and once with water. The organic phase was dried over sodium sulphate and evaporated to dryness at reduced pressure. The crude oil obtained was purified by chromatography on silica gel in the 98/2 dichloromethane/methanol eluent mixture. After evaporation to dryness and drying in vacuum 53 g of methyl ester of N-(2-mercaptoethyl) malonamic acid were obtained in the form of a colorless oil.

The 200 MHz $^1$H NMR spectrum ($CDCl_3$+TMS) and the thiol determination were consistent with the expected structure.

b) N-(2-Mercaptoethyl)malonamide 31 g of methyl ester of N-(2-mercapto-ethyl)malonamic acid obtained in Example 3a) were added to 220 cm³ of aqueous 20% solution of aqueous ammonia, with stirring, while the temperature was kept below or equal to 30° C. Stirring was continued for 1 hour at ambient temperature. A slight cloudiness was removed by filtration on sintered glass. The filtrate was evaporated to dryness at reduced pressure. The solid obtained was recrystallized from ethyl acetate. After filtering and drying in vacuum at 50° C., 27 g of N-(2-mercaptoethyl)malonamide were obtained in the form of a white solid with a melting point of 100° C.

The 200, MHz $^1$H NMR spectrum (DMSO-$d_6$+TMS) was consistent with the expected structure. The thiol determination was also consistent: found: 6.12 meq./g; calculated: 6.17 meq./g.

ELEMENTAL ANALYSIS: $C_5H_{10}N_2O_2S$

|            | C %   | H %  | N %   | O %   | S %   |
|------------|-------|------|-------|-------|-------|
| Calculated | 37.02 | 6.21 | 17.27 | 19.73 | 19.77 |
| Found      | 37.10 | 6.22 | 17.01 | 19.87 | 19.52 |

EXAMPLE 4

Preparation of N-(2-mercaptoethyl)glutararide a) Methyl ester of N-(2-mercaptoethyl)glutaramic acid The procedure was the same as in Example 1a), using:

6.2 g (54 nmol) of cysteamine hydrochloride 7.7 cm³ of triethanolamine 7.3 g of 1-hydroxybenzotriazole 11.3 g of dicyclohexylcarbodiimide 8.4 g (57 mmol) of monomethyl glutarate.

9.1 g of methyl ester of N-(2-mercaptoethyl)glutaramic acid were obtained in the form of a white solid.

The 200 MHz $^1$H NMR spectrum ($CDCl_3$+TMS) and the thiol determination were consistent with the expected structure.

b) N-(2-Mercaptoethyl)glutaramide

A solution of 9.1 g (44 mmol) of methyl ester of N-(2-mercaptoethyl)glutaramic acid obtained in Example 4a), in 100 cm³ of aqueous 20% solution of aqueous ammonia was stirred for 4 hours at ambient temperature under argon atmosphere. After evaporation to dryness and recrystallization from isopropanol 7 g of N-(2-mercaptoethyl) glutaramide were obtained in the form of a white solid with a melting point of 127° C.

The 200 MHz $^1$H NMR spectrum (DMSO-$d_6$+TMS) was consistent with the expected structure. The thiol determination was also consistent: found: 5.10 meq./g; calculated: 5.26 meq./g.

ELEMENTAL ANALYSIS: $C_7H_{14}N_2O_2S$

|            | C %   | H %  | N %   | O %   | S %   |
|------------|-------|------|-------|-------|-------|
| Calculated | 44.20 | 7.42 | 14.72 | 16.82 | 16.85 |
| Found      | 43.70 | 7.51 | 14.66 | 17.39 | 16.74 |

EXAMPLE 5

Preparation of the disulphide of N(2-mercaptoethyl) succinamide 20 g (0.113 mol) of N-(2-mercaptoethyl)succinamide obtained in Example 1b) were dissolved in 1 liter of methanol. 6 cm³ of aqueous 30% hydrogen peroxide were added dropwise at ambient temperature to the solution obtained, followed by 50 mg of ferrous sulphate. The disulphite precipitates as it was being formed. After stirring overnight the mixture was cooled to +5° C. and filtered on No. 3 sintered glass. The crude disulphide was purified by recrystallization from an ethanol/water mixture. After filtering and drying in vacuum at 40–50° C., 12 g of disulphide of N-(2-mercapto-ethyl)succinamide were thus obtained in the form of a white solid with a melting point of 218° C.

The 200 MHz $^1$H NMR (DMSO+TMS) and 50 MHz $^{13}$C (DMSO+TMS) spectra were consistent with the expected structure.

ELEMENTAL ANALYSIS: $C_{12}H_{22}N_4O_4S_2$

|            | C %   | H %  | N %   | O %   | S %   |
|------------|-------|------|-------|-------|-------|
| Calculated | 41.13 | 6.33 | 15.99 | 18.26 | 18.36 |
| Found      | 40.90 | 6.19 | 15.76 | 18.61 | 18.14 |

EXAMPLE 6

A reducing composition for permanent deformation of hair was prepared according to the invention by mixing the following ingredients:

| Compound of Example 1 | | 10 g |
|---|---|---|
| N-laurylamidopropylbetaine sold under the name "Softazoline LPB" by the company Kawaken Fine Chemicals | | 0.35 g |
| Monoethanolamine | q.s. | pH 8.4 |
| Perfume | q.s. | |
| Demineralized water | q.s. | 100 g |

This composition was applied to wetted hair previously wound onto hair-setting rollers. After the composition was allowed to act for approximately 15 minutes, it was rinsed copiously with water and the following oxidizing composition was then applied:

| | | |
|---|---|---|
| Aqueous hydrogen peroxide (i.e., 2.4% by weight of the composition) | q.s. | 8 volumes |
| Stabilizers | q.s. | |
| Lauryldimethylamine oxide | | 0.7 g |
| Perfume | | |
| Lactic acid | q.s. | pH 3.0 |
| Demineralized water | q.s. | 100 g |

The oxidizing composition was allowed to act for approximately 10 minutes and the rollers were then removed and the hair was rinsed copiously with water.

After drying under a hood the hair was beautifully curly.

EXAMPLE 7

According to the same embodiment as in Example 1, a permanent deformation of hair was carried out with the aid of the following reducing and oxidizing compositions:

| | | |
|---|---|---|
| A - Reducing composition | | |
| Compound of Example 1 | | 8.5 g |
| Cocoamidopropylbetaine | | 1 g |
| Ammonium carbonate | | 2 g |
| Aqueous ammonia | q.s | pH 9 |
| Demineralized water | q.s | 100 g |
| B - Oxidizing composition | | |
| Sodium bromate | | 8 g |
| Triethanolamine | q.s. | pH 8.0 |
| Monosodium phosphate hydrate (12 $H_2O$) | | 0.3 g |
| Trisodium phosphate hydrate (2 $H_2O$) | | 0.5 g |
| Cocoylamidopropylbetaine with coprah monoglyceride sold under the name of "Tegobetaine HS" by the Goldschmidt company | | 1 g |
| Demineralized water | q.s | 100 g |

EXAMPLE 8

| | | |
|---|---|---|
| A - Reducing composition | | |
| Compound of Example 1 | | 9.5 g |
| Cetyltrimethylammonium chloride | | 0.5 g |
| Glycerol | | 2 g |
| Triethanolamine | q.s. | pH 7.9 |
| Demineralized water | q.s. | 100 g |
| B - Oxidizing composition | | |
| 200-volume aqueous hydrogen | | 4.8 g |
| 8-Hydroxyquinoline sulphate | | 0.01 g |
| Phenacetin | | 0.05 g |
| Citric acid | q.s. | pH 3.0 |
| Perfume | q.s. | |
| Demineralized water | q.s. | 100 g |

EXAMPLE 9

The following reducing composition was applied to European hair wound onto rollers 9 mm in diameter:

| | | |
|---|---|---|
| Compound of Example 2 | | 16 g |
| Aqueous ammonia | q.s. | pH 9 |
| N-Laurylpropylbetaine | | 1 g |
| Perfume | q.s | |
| Demineralized water | q.s | 100 g |

This was applied at ordinary temperature for 20 minutes. After rinsing the oxidizing composition of Example 6 was applied.

After 5 minutes' application the hair was rinsed and unwound.

After drying, the hair was beautifully curly and had good cosmetic properties.

EXAMPLE 10

The following reducing composition was applied to European hair wound onto rollers 9 mm in diameter:

| | | |
|---|---|---|
| Compound of Example 3 | | 10 g |
| Monoethanolamine | q.s. | pH 9.2 |
| Cocoamidopropylbetaine | | 1 g |
| Perfume | q.s. | |
| Demineralized water | q.s. | 100 g |

This was applied at ordinary temperature for 20 minutes. After rinsing, the oxidizing composition of Example 6 was applied.

After 5 minutes' application the hair was rinsed and unwound.

After drying, the hair was beautifully curly and had good cosmetic properties.

EXAMPLE 11

The following reducing composition was applied to European hair wound onto rollers 9 mm in diameter:

| | | |
|---|---|---|
| Compound of Example 2 | | 10 g |
| Ammonium carbonate | | 2 g |
| Monoethanolamine | q.s. | pH 9 |
| Cocoamidopropylbetaine | | 1 g |
| Perfume | q.s | |
| Demineralized water | q.s. | 100 g |

This was applied at ordinary temperature for 20 minutes. After rinsing, the oxidizing composition of Example 6 was applied.

After 5 minutes' application the hair was rinsed and unwound.

After drying, the hair was beautifully curly and had good cosmetic properties.

EXAMPLE 12

The following reducing composition was applied to European hair wound onto rollers 9 mm in diameter:

| | | |
|---|---|---|
| Compound of Example 3 | | 10 g |
| Compound of Example 5 | | 3 g |
| Aqueous ammonia | | 2 g |
| Ammonium carbonate | | 1 g |
| Monoethanolamine | q.s. | pH 9.2 |
| Cetyltrimethylammonium chloride | | 1 g |
| Perfume | q.s. | |
| Demineralized water | q.s. | 100 g |

This was applied at ordinary temperature for 20 minutes. After rinsing, the oxidizing composition of Example 6 was applied.

After 5 minutes' application the hair was rinsed and unwound.

After drying, the hair was beautifully curly and had good cosmetic properties.

EXAMPLE 13

The following reducing composition was applied to European hair wound onto rollers 9 mm in diameter:

| | | |
|---|---|---|
| Compound of Example 2 | | 12 g |
| Acetic acid | | 0.2 g |
| Monoethanolamine | q.s. | pH 7.3 |
| Cocoamidopropylbetaine | | 1 g |
| Perfume | q.s. | |
| Demineralized water | q.s. | 100 g |

This was applied at ordinary temperature for 20 minutes. After rinsing, the oxidizing composition of Example 6 was applied.

After 5 minutes' application the hair was rinsed and unwound.

After drying, the hair was beautifully curly and had good cosmetic properties.

What is claimed is:

1. A cosmetic composition for the first step of an operation for permanent deformation of hair wherein disulphide bonds of keratin are reduced, the composition comprising at least one compound having the following formula:

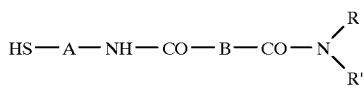  (I)

in which:

A denotes the divalent radical $-(CH_2)_n-$, n being an integer from 2 to 5, or the divalent radical $-(CH_2)_2-O-(CH_2)_2-$, B denotes a radical, said radical being:
(a) the divalent radical $-(CH_2)_m-$, m being an integer from 1 to 7,
(b) the divalent radical

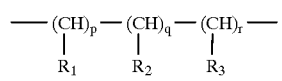

in which one of the groups $R_1$, $R_2$ and $R_3$ denotes a radical, said radical being a linear or branched alkyl radical containing from 1 to 4 carbon atoms, methoxymethyl, phenyl, benzyl, cyclohexyl or cyclopentyl, and the other two groups are a hydrogen atom, p, q and r being 0 or an integer from 1 to 4 wherein $1<p+q+r<4$, and further wherein the p, q, or r corresponding to that radical $R_1$, $R_2$ or $R_3$ which is not a hydrogen atom is an integer from 1 to 4,
(c) the divalent radical

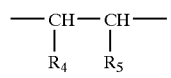

in which $R_4$ and $R_5$ either, being identical or different, denote a linear or branched alkyl radical containing from 1 to 4 carbon atoms, or, together with the adjacent carbon atoms, form a cyclohexane or cyclohexene ring, (d) the divalent radical

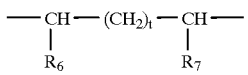

in which one of $R_6$ and $R_7$ denotes an $-NH_2$ radical and the other denotes a hydrogen atom; t being equal to 0 or 1, or
(e) the divalent radical

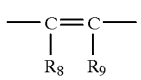

in which $R_8$ and $R_9$ either, being identical or different, denote a hydrogen atom or a linear or branched alkyl radical containing from 1 to 4 carbon atoms or, together with the adjacent carbon atoms, form a benzene ring, R and R', which are identical or different, denote:
either a hydrogen atom or a radical, said radical being a linear or branched alkyl radical containing from 1 to 4 carbon atoms or a linear or branched hydroxyalkyl radical containing from 1 to 5 carbon atoms,
or R denotes a hydrogen atom and R' denotes an aminoalkyl radical $-(CH_2)_v-NR_{10}R_{11}$, in which v is an integer from 1 to 3 and $R_{10}$ and $R_{11}$, which are identical or different, denote a hydrogen atom or a linear or branched alkyl radical containing from 1 to 3 carbon atoms, $R_{10}$ and $R_{11}$ being incapable of simultaneously denoting a hydrogen atom, or an organic salt or an inorganic salt of said at least one compound of formula (I), and a cosmetically acceptable carrier;
wherein said cosmetic composition additionally contains a cosmetically effective amount of at least one surface-active agent selected from nonionic, anionic, cationic or amphoteric surface active agents.

2. The composition according to claim 1, wherein the salt of the compound of formula (I) is a hydrochloride, a hydrobromide, a citrate, an oxalate or an acetate.

3. The composition according to claim 1, wherein when, in the formula (I), B denotes the $-CH_2-$ divalent radical, the compound is an:
N-(2-mercaptoethyl)malonamide
N-(3-mercaptopropyl)malonamide
N-(5-mercaptopentyl)malonamide
N-[2-(2-mercaptoethoxy)ethyl]malonamide
N-(2-mercaptoethyl)-N'-methylmalonamide
N-(2-mercaptoethyl)-N',N'-dimethylmalonamide
N-(2-mercaptoethyl)-N'-ethylmalonamide
N-(2-mercaptoethyl)-N',N'-diethylmalonamide
N-(2-mercaptoethyl)-N'-(2-hydroxyethyl)malonamide
N-(2-mercaptoethyl)-N', N'-(2,2-dihydroxyethyl) malonamide
N-(2-mercaptoethyl)-N'-(3-dimethylaminopropyl) malonamide
N-(2-mercaptoethyl)-N'-(3-diethylaminopropyl) malonamide.

4. The composition according to claim 1, wherein when, in the formula (I), B denotes the $-(CH_2)_2-$ divalent radical, the compound is an:
N-(2-mercaptoethyl)succinamide
N-(3-mercaptopropyl)succinamide N-(5-mercaptopentyl)succinamide N-[(2-(2-mercaptoethoxy) ethyl ]succinamide N-(2-mercaptoethyl)-N'-methylsuccinamide N-(2-mercaptoethyl)-N',N'-dimethylsuccinamide N-(2-mercaptoethyl)-N'-ethylsuccinamide N-(2-mercaptoethyl)-N',N'-diethylsuccinamide N-(2-mercaptoethyl)-N'-(2-hydroxyethyl)succinamide N-(2-mercaptoethyl)-N', N'-(2,2-dihydroxyethyl) succinamide N-(2-mercaptoethyl)-N'-(3-dimethylaminopropyl) succinamide or N-(2-mercaptoethyl)-N'-(3-diethylaminopropyl) succinamide.

5. The composition according to claim 1, wherein when, in the formula (I), B denotes the —(CH$_2$)$_3$— divalent radical, the compound is an:

N-(2-mercaptoethyl)glutaramide

N-(3-mercaptopropyl)glutaramide

N-(5-mercaptopentyl)glutaramide

N-[2-(2-mercaptoethoxy)ethyl]glutaramide

N-(2-mercaptoethyl)-N'-methylglutaramide

N-(2-mercaptoethyl)-N',N'-dimethylglutaramide

N-(2-mercaptoethyl)-N'-ethylglutaramide

N-(2-mercaptoethyl)-N',N'-diethylglutaramide

N-(2-mercaptoethyl)-N-(2-hydroxyethyl)glutaramide

N-(2-mercaptoethyl)-N',N'-(2,2-dihydroxyethyl) glutaramide or

N-(2-mercaptoethyl)-N'-(3-dimethylaminopropyl) glutaramide.

6. The composition according to claim 1, wherein when, in the formula (I), B denotes the —(CH$_2$)$_4$— divalent radical, the compounds are anm:

N-(2-mercaptoethyl)adipamide

N-(2-mercaptoethyl)-N'-methyladipamide

N-(2-mercaptoethyl)-N',N'-dimethyladipamide

N-(2-mercaptoethyl)-N'-ethyladipamide

N-(2-mercaptoethy)-N'-(2-hydroxyethyl)adipamide

N-(2-mercaptoethyl)-N',N'-(2,2-dihydroxyethyl) adipamide or

N-(2-mercaptoethyl)-N'-(3-dimethylaminopropyl) adipamide.

7. The composition according to claim 1, wherein, in the formula (I) B denotes the divalent radical

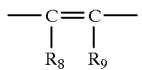

R$_8$ and R$_9$ having the same meanings as those given in claim 1, the compound is an:

N-(2-mercaptoethyl)fumaramide

N-(3-mercaptopropyl)fumaramide

N-(5-mercaptopentyl)fumaramide

N-[2-(2-mercaptoethoxy)ethyl]fumaramide

N-(2-mercaptoethyl)-N'-methylfumaramide

N-(2-mercaptoethyl)-N',N'-dimethylfumaramide

N-(2-mercaptoethyl)-N'-ethylfumaramide

N-(2-mercaptoethyl)-N',N'-diethylfumaramide

N-(2-mercaptoethyl)-N'-(2-hydroxyethyl)fumaramide

N-(2-mercaptoethyl)-N',N'(2,2-dihydroxyethyl) fumaramide

N-(2-mercaptoethyl)-N'-(3-dimethylaminopropyl) fumaramide;

N-(2-mercaptoethyl)terephthalamide

N-(2-mercaptoethyl)-N'-methylterephthalamide

N-(2-mercaptoethyl)-N'-ethylterephthalamide

N-(2-mercaptoethyl)-N'-(2-hydroxyethyl) terephthalamide or

N-(2-mercaptoethyl)-N'-(3-dimethylaminopropyl) terephthalamide.

8. The composition according to claim 1, wherein when, in the formula (I), B denotes the divalent radical —(CH$_2$)$_m$—, m being an integer equal to 6 or 7, the compound is an:

octanedioic acid 1-amide 5-[(2-mercaptoethyl)amide] or nonanedioic acid 1-amide 5-[(2-mercaptoethyl)amide].

9. The composition according to claim 1, wherein when, in the formula (I), B denotes the divalent radical

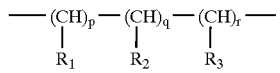

R$_1$, R$_2$, R$_3$, p, q and r having the same meanings as those given in claim 1, the compounds are an:

3-methylpentanedioic acid 1-amide 5-[(2-mercaptoethyl) amide] or 2-ethylhexanedioic acid 1-amide 6-[(2-mercaptoethyl) amide].

10. The composition according to claim 1, wherein when, in the formula (I), B denotes the divalent radical

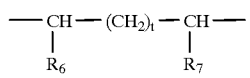

R$_6$, R$_7$ and t having the same meanings as those given in claim 1, the compound is an:

4-aminopentanedioic acid 1-amide 5-[(2-mercaptoethyl) amide] or 3-aminobutanedioic acid 1-amide 5-[(2-mercaptoethyl) amide].

11. The composition according to claim 1, wherein the compound of formula (I) is present in a concentration ranging from 0.5% to 30% relative to the total weight of the composition.

12. The composition according to claim 11, wherein the compound of formula (I) is present in a concentration ranging from 5% to 20% relative to the total weight of the composition.

13. The composition according to claim 1, wherein said composition contains an alkaline agent, said alkaline agent being aqueous ammonia, monoethanolamine, diethanolamine, triethanolamine, 1.3-propanediamine, ammonium carbamate, an alkali metal carbonate, an alkali metal bicarbonate, ammonium carbonate, ammonium bicarbonate, an organic carbonate, or an alkali metal hydroxide, in an amount effective to provide said composition with a pH ranging from 4 to 11.

14. The composition according to claim 1, wherein said composition contains an acidifying agent, said acidifying agent being hydrochloric acid, acetic acid, lactic acid, oxalic acid, or boric acid, in an amount effective to provide said composition with a pH ranging from 4 to 11.

15. The composition according to claim 13, wherein said composition has a pH ranging from 6 to 10.

16. The composition according to claim 14, wherein said composition has a pH ranging from 6 to 10.

* * * * *

UNITED STATES PATENT AND TRADEMARK OFFICE
CERTIFICATE OF CORRECTION

PATENT NO. : 5,935,558
DATED : August 10, 1999
INVENTOR(S) : MALLE

It is certified that error appears in the above-indentified patent and that said Letters Patent is hereby corrected as shown below:

Claim 1, col. 17, line 53, "$1<p+q+r<4$" should read --$1 \leq p+q+r \leq 4$--.

Claim 3, col. 18, line 60, insert --or-- after "malonamide".

Claim 5, col. 19, line 27, delete "N" (second occurrence) and insert --N'--.

Signed and Sealed this

First Day of February, 2000

Attest:

Q. TODD DICKINSON

Attesting Officer

Acting Commissioner of Patents and Trademarks